(12) United States Patent
Buchholz et al.

(10) Patent No.: US 7,671,217 B2
(45) Date of Patent: Mar. 2, 2010

(54) METHOD FOR THE DECARBOXYLATION OF DICARBOXYLIC ACIDS

(75) Inventors: Sigurd Buchholz, Köln (DE); Alexander Klausener, Pulheim (DE); Reinhard Langer, Tönisvorst (DE); Leslaw Mleczko, Dormagen (DE); Günter Rauchschwalbe, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 10/538,995

(22) PCT Filed: Dec. 4, 2003

(86) PCT No.: PCT/EP03/13679

§ 371 (c)(1), (2), (4) Date: Dec. 20, 2005

(87) PCT Pub. No.: WO2004/055023

PCT Pub. Date: Jul. 1, 2004

(65) Prior Publication Data

US 2006/0149083 A1    Jul. 6, 2006

(30) Foreign Application Priority Data

Dec. 16, 2002    (DE) .................................. 102 58 588

(51) Int. Cl.
*C07D 495/02* (2006.01)
(52) U.S. Cl. ....................................................... 549/50
(58) Field of Classification Search .................... 549/50
See application file for complete search history.

(56) References Cited

U.S. PATENT DOCUMENTS 2,453,103 A    11/1948    Turnbull, Jr. ................ 260/329

2001/0034453 A1 *    10/2001    Rauchschwalbe et al. ..... 549/50

FOREIGN PATENT DOCUMENTS

DE    100 29 078    12/2001

OTHER PUBLICATIONS

Merz et al. "Improved Preparation of 3,4-Dimethoxythiophene" Journal fur praktische Chemie, 1996, vol. 338, pp. 672-674.*
Coffey et al.,(thermal decarboxylation of_the molten material); Synthetic Communications, 26(11), 2205-2212, 1996 "A Facile Synthesis of 3,4-Dialkoxythiophenes".
Stephan et al., (decarboxylation at 180° C with addition of chromium(III)-copper(II) oxide) Journal of Electroanalytical Chemistry, 443, 217-226, 1998, "Electrochemical behaviour of 3,4-ethylenedioxythiophene functionalized by a sulphonate group. Application to the preparation of poly(3,4-ethylenedioxythiophene) having permanent cation-exchange properties".
Merz and Rehm; (without catalyst or diluent) Journal für Praktische Chemie, 228, 672-674, 1996; "Improved Preparation of 3,4-Dimethoxythiophene".
Overberger C G et al: "The Preparation of 3,4-Dimethoxy-2,5-Dicarbethoxy-Thiopene. 3,4 Dimethoxythiophene" Journal of the American Chemical Society, American Chemical Society, Washington, DC, US, Bd. 73, 1951, Seiten 2956-2957, XP001005623 ISSN: 0002-7863 das ganze dokument.

* cited by examiner

*Primary Examiner*—Joseph R Kosack
(74) *Attorney, Agent, or Firm*—Michael A. Miller

(57) ABSTRACT

The invention relates to a method for the thermal decarboxylation of dicarboxylic acids, in particular to 3,4-ethylene dioxythiophene-2,5-dicarboxylic acid as an educt. According to said method the educt is used in solid form and/or the reaction is carried out in the presence of a plurality of fluidised bed bodies. No solvents are used in the reaction and the decarboxylation product that is formed during the reaction is carried away from the reaction zone in gaseous form.

11 Claims, No Drawings

METHOD FOR THE DECARBOXYLATION OF DICARBOXYLIC ACIDS

The invention relates to a process for the thermal decarboxylation of dicarboxylic acids, in particular the decarboxylation of dialkoxythiophenedicarboxylic acids and alkylenedioxythiophenedicarboxylic acids without addition of an additional solvent, if appropriate with addition of an inert gas.

For the purposes of the present invention, inert gases are gases which do not undergo any reaction with the dicarboxylic acid under the conditions employed.

Various methods of decarboxylating monocarboxylic and polycarboxylic acids are known. According to U.S. Pat. No. 2,453,103, the thermal decarboxylation of 3,4-dimethoxythiophene-2,5-dicarboxylic acid is carried out with addition of a pulverulent copper catalyst. Similar procedures for the decarboxylation of dialkoxythiophenedicarboxylic acids and alkylenedioxythiophenedicarboxylic acids are described, for example, by Coffey et al. (thermal decarboxylation of the molten material, in: Synthetic Communications, 26(11), 2205-2212, 1996), by Stéphan et al. (decarboxylation at 180° C. with addition of chromium(III)-copper(II) oxide, in: Journal of Electroanalytical Chemistry, 443, 217-226, 1998) or Merz and Rehm (without catalyst or diluent, in: Journal für Praktische Chemie, 228, 672-674, 1996). The conditions employed in these processes usually take account of the thermal instability of the compounds. Thus, the decarboxylation is advantageously carried out in a solvent with addition of a catalyst which accelerates the decarboxylation. The decarboxylation of 3,4-ethylenedioxythiophene-2,5-dicarboxylic acid to form 3,4-ethylenedioxythiophene is thus carried out in an organic solvent (for example tetrahydrothiophene 1,1-dioxide) with addition of a copper carbonate as catalyst at temperatures of 100-200° C. and pressures of 800-1200 hPa. In this way of carrying out the process, all of the starting material is firstly decarboxylated and the product is then distilled from the solvent under reduced pressure. However, in addition to the 3,4-ethylenedioxythiophene-2,5-dicarboxylic acid, the starting material always contains small amounts of by-products which are formed in previous steps in the synthesis. These by-products accumulate in the solvent and limit the reusability of solvent and catalyst. Cu-containing waste is formed and has to be disposed of, which costs money. Furthermore, the process described for the decarboxylation of 3,4-ethylenedioxythiophene-2,5-dicarboxylic acid, which represents the prior art, can be operated only batchwise. In the purely thermal decarboxylation, a large part of the product remains in the reaction space and, owing to the elevated temperatures, there is increased formation of by-products which have a severe adverse effect on the quality or make complicated subsequent purification necessary.

It is an object of the present invention to develop a procedure for the decarboxylation of 3,4-ethylenedioxythiophene-2,5-dicarboxylic acid and similar dicarboxylic acids which makes a continuous or pseudocontinuous mode of operation possible while simultaneously minimizing the use of auxiliaries (solvent and catalyst).

The invention achieves this object by means of a process for the thermal decarboxylation of dicarboxylic acids, in particular 3,4-ethylenedioxythiophene-2,5-dicarboxylic acid, as starting material, characterized in that the starting material is used as a solid and/or the reaction is carried out in the presence of a plurality of fluidized-bed bodies, with the reaction being carried out in the absence of solvents and the decarboxylation product formed in the reaction, in particular 3,4-ethylenedioxythiophene, being discharged from the reaction zone in gaseous form.

The decarboxylation is preferably carried out at a temperature of from 100 to 600° C., more preferably from 100 to 500° C., particularly preferably from 150 to 400° C.

In experiments on the purely thermal decarboxylation of 3,4-ethylene-dioxythiophene-2,5-dicarboxylic acid in a fluidized bed, it has surprisingly been found that 3,4-ethylenedioxythiophene can be obtained in very high selectivities even in the absence of a solvent by heterogeneous reaction of the solid starting material alone. It is found that the 3,4-ethylenedioxythiophene formed has a sufficiently high vapor pressure at the temperature necessary for the decarboxylation to be able to be discharged in gaseous form together with an inert gas stream and be able to be precipitated by cooling. In this way, the use of auxiliaries is minimized and continuous or pseudocontinuous operation is made possible.

The process of the invention can be carried out in various types of reactor, as long as the product formed by means of the decarboxylation, e.g. 3,4-ethylene-dioxythiophene, can be discharged from the reactor in gaseous form. Examples which may be mentioned here are fixed-bed reactors, moving-bed reactors, reactors containing a bubble-forming, turbulent or jet-permeated fluidized bed, internally or externally circulating fluidized beds. It is also possible to introduce the starting material, e.g. 3,4-ethylenedioxythiophene-2,5-dicarboxylic acid, into a reactor filled with fluidized bed bodies which, for example, comes under the abovementioned classes.

In particular, the process is carried out continuously in a bubble-forming or turbulent or jet-permeated fluidized bed, or in an internally or externally circulating fluidized bed.

The reaction is particularly preferably carried out in the presence of an inert auxiliary gas, in particular a gas selected from the group consisting of noble gases, nitrogen, water vapor, carbon monoxide and carbon dioxide and mixtures of various such inert auxiliary gases.

Possible inert gases include all gases which do not react with the starting material or product under the reaction conditions selected; suitable inert gases, for example, noble gases, nitrogen, water vapor, carbon monoxide or carbon dioxide. It is possible to carry out the process of the invention for the decarboxylation of 3,4-ethylenedioxythiophene-2,5-dicarboxylic acid with addition of an inert gas or a mixture of a plurality of inert gases in any combination.

The temperature can, as described, be varied within the temperature range from 100° C. to 600° C. However, it has to be high enough for the decarboxylation of the starting material, e.g. 3,4-ethylenedioxythiophene-2,5-dicarboxylic acid, to be achieved and must not exceed the decomposition temperature of 3,4-ethylene-dioxythiophene-2,5-dicarboxylic acid or 3,4-ethylenedioxythiophene.

The reaction is preferably carried out in a fluidized-bed reactor in which fluidized bed bodies having a mean diameter (number average) greater than the particle diameter of the dicarboxylic acid are used.

The fluidized bed bodies particularly preferably have a solids density $\rho_s$ of $0.5 \text{ g·cm}^{-3} < \rho_s < 6 \text{ g·cm}^{-3}$.

The fluidized bed bodies can also preferably be used as heat transfer media which are preheated outside the reaction zone and circulated through the reaction zone.

The fluidized bed bodies preferably consist partly or entirely of a catalytically active material, in particular copper or a copper salt, preferably $CuCO_3$.

The process of the invention is preferably carried out in a fluidized bed. For this purpose, solid particles of 3,4-ethylenedioxythiophene-2,5-dicarboxylic acid, hereinafter referred to as particles, are placed in the reaction space. The particles can be introduced batchwise or continuously from the outside. The particles form a fixed bed through which the gas fed in is passed. The inflow velocity of the gas fed in can be set so that the fixed bed is fluidized and a fluidized bed is formed. The appropriate procedure is known per se to those skilled in the art. The inflow velocity of the gas fed in has to correspond at least to the loosening velocity (also referred to as minimum fluidization velocity). For the present purposes the loosening velocity is the velocity at which a gas flows through a bed of particles and below which the fixed bed is retained, i.e. below which the bed particles remain largely stationary. Above this velocity, fluidization of the bed commences, i.e. the bed particles move and the first bubbles are formed. In operation of a bubble-forming fluidized bed, the gas velocity is selected so that it corresponds to from one to ten times the loosening velocity, preferably from one to seven times the loosening velocity, particularly preferably from one to five times the loosening velocity.

If the starting material is present in a very fine particle fraction, then interparticulate forces predominate and the solids are difficult to handle. In this case, it can be advantageous to introduce the 3,4-ethylenedioxythiophene-2,5-dicarboxylic acid starting material into a bed of relatively coarse particles. If the mean particle size of the 3,4-ethylenedioxythiophene-2,5-dicarboxylic acid is, for example, 0.1-50 μm, then the handling in a bed containing particles having a mean particle diameter dP of 50<dP<350 μm can be made considerably easier. These relatively coarse bed particles preferably have a solids density $\rho s$ of 0.5 $g \cdot cm^{-3} < \rho s$ 4 $g \cdot cm^{-3}$. These described particles act as carriers for the small particles which adhere to the surface. Furthermore, the initially charged bed particles can serve as momentum carriers and heat transfer media and/or consist entirely or partly of a catalytically active material. As catalytically active materials, it is possible to use, for example, metals, metal oxides or metal salts. Particular preference is given to using copper, copper oxides and copper salts. It is possible to use all-active materials, but the active components can also be mixed with or applied to a support. The use of pure components or of mixtures is conceivable. The 3,4-ethylenedioxythiophene-2,5-dicarboxylic acid starting material can be introduced, for example, by means of screws, injectors or a lock system. A further method of introduction is the spraying-in of molten 3,4-ethylenedioxythiophene-2,5-dicarboxylic acid or 3,4-ethylenedioxythiophene-2,5-dicarboxylic acid which has been diluted with a solvent.

The introduction of a catalyst in pure form, as a mixture or in supported form can also be effected in the form of internals in the reactor. Examples which may be mentioned are rigid or flexible internals, rod- and tube-shaped internals, constructions in the form of perforated metal sheets, meshes, grids or three-dimensional structures and also packing and the use of shaped bodies or free-flowing elements.

The separation of finely-divided solids starting material from the gas stream leaving the reactor can be effected, for example, by means of a cyclone, a filter or a gas scrubber. It is preferably separated off by means of a cyclone and/or a filter. The collected solids starting material is advantageously recirculated to the decarboxylation step. This recirculation can be effected, for example, by means of internal or external circulation. However, recirculation can also be carried out by back-blowing and cleaning of filters.

A preferred process is characterized in that any solid carried out from the reaction zone by the gas stream is separated off from the product by means of a cyclone and/or filter.

Preference is likewise given to a variant of the process in which the unreacted solid starting material which has been circulated off from the product gas stream is recirculated either batchwise or continuously to the reaction zone.

The process of the invention is illustrated below with the aid of some examples, but the examples are not to be regarded as restricting the scope of the invention.

EXAMPLES

Example 1

Fixed Bed 4 g of dried crude 3,4-ethylenedioxythiophene-2,5-dicarboxylic acid were placed in a glass reactor (diameter: 16 mm, total height: 400 mm) and heated to a maximum reaction temperature of 300° C. (heating rate: 2° C./min) in a stream of nitrogen. The starting material was reacted over a time of 80 minutes. Of the 4 g ($1.7 \times 10^{-2}$ mol) initially introduced, 3.5 g ($1.52 \times 10^{-2}$ mol) had reacted and a small proportion was carried out from the reactor by means of the nitrogen stream. 2.89 g of a product mixture of 3,4-ethylenedioxythiophene-2,5-dicarboxylic acid and 3,4-ethylenedioxythiophene were collected in a downstream cold trap. The 3,4-ethylenedioxythiophene content determined by HPLC was >90% by weight.

Example 2

Fluidized Bed, Jet-Driven Bed Reactor 120.0 g (0.52 mol) of dried crude 3,4-ethylenedioxythiophene-2,5-dicarboxylic acid were placed in a glass reactor (diameter: 50 mm, total height: 730 mm, conical gas inlet with a 10 mm gas distributor frit) and heated to a maximum reaction temperature of 320° C. (heating rate: 2° C./min) in a stream of nitrogen (normal conditions). The starting material was reacted over a time of 100 minutes. 32.0 g (0.139 mol) of the crude starting material had reacted. 16.6 g of product were condensed out in a downstream cold trap. The 3,4-ethylenedioxythiophene content was >94% by weight.

Example 3

"Particle Powder" Fluidized Bed 3000 g of silica sand having a diameter of 160-250 mm were placed in a glass reactor (diameter: 95 mm, total height: 700 mm, gas distributor frit: 95 mm) with an additional gas distributor and heated to a reaction temperature of 280° C. in the silica bed with fluidization by means of nitrogen. A mixture of 0.1351 mol of 3,4-ethylenedioxythiophene-2,5-dicarboxylic acid and basic copper carbonate in a mass ratio of 1:1 was introduced into the nitrogen-fluidized reactor over a time of 58 minutes. The decarboxylation proceeded there and the product was condensed in a plurality of cold traps connected in series. The yield was Y=83 mol % at a product purity determined by HPLC of more than 94% by weight. The solid discharged from the reactor and separated off in a cyclone can be reused as starting material.

The invention claimed is:

1. A process for the thermal decarboxylation of 3,4-ethylenedioxythiophene-2,5-dicarboxylic acid as starting material, comprising:
    reacting the starting material as a solid in the presence of a plurality of fluidized-bed bodies, and wherein the reaction is carried out in the absence of solvents, and
    discharging the decarboxylation product formed in the reaction from the reaction zone in gaseous form.

2. The process as claimed in claim 1, wherein the decarboxylation is carried out at a temperature of from 100 to 600° C.

3. The process according to claim 1, wherein the process is carried out continuously in a bubble-forming, turbulent, jet-permeated fluidized bed or in an internally or externally circulating fluidized bed.

4. The process as claimed in claim 1 wherein the reaction is carried out in the presence of an inert auxiliary gas selected from the group consisting of noble gases, nitrogen, water vapor, carbon monoxide, carbon dioxide and mixtures thereof.

5. The process as claimed in claim 1 wherein the reaction is carried out in a fluidized-bed reactor in which fluidized bed bodies having a mean diameter (number average) greater than the particle diameter of the dicarboxylic acid.

6. The process according to claim 5, wherein the fluidized bed bodies have a solids density $\rho_s$ of 0.5 g·cm$^{-5}$<$\rho_s$<6 g·cm$^{-3}$.

7. The process according to claim 1 wherein the fluidized bed bodies are used as heat transfer media wherein the fluidized bed bodies are preheated outside the reaction zone and circulated through the reaction zone and comprise a catalytically active material.

8. The process according to claim 7, wherein the catalytically active material of the fluidized bed bodies comprises copper or a copper salt.

9. The process according to claims 1 wherein any solid carried out from the reaction zone by the gas stream is separated off from the product by means of a cyclone and/or filter.

10. The process according to claims 1 wherein the unreacted solid starting material separated off from the product gas steam is recirculated batchwise or continuously to the reaction zone.

11. The process according to claim 8 wherein the catalytically active material of the comprised $CuCO_3$.

* * * * *